United States Patent [19]
Daley et al.

[11] Patent Number: 5,336,488
[45] Date of Patent: Aug. 9, 1994

[54] METHOD OF TREATING OR PREVENTING MASTITIS IN ANIMALS WITH INVOLUTING MAMMARY GLANDS BY ADMINISTERING RECOMBINANT CYTOKINES

[75] Inventors: Michael J. Daley, Yardley, Pa.; Gary J. Furda, Trenton, N.J.; Phillip W. Hayes, Rushland, Pa.

[73] Assignee: American Cyanamid Company, Wayne, N.J.

[21] Appl. No.: 905,969

[22] Filed: Jun. 29, 1992

Related U.S. Application Data

[62] Division of Ser. No. 741,278, Aug. 7, 1991.

[51] Int. Cl.$^5$ ............................................. A61K 37/02
[52] U.S. Cl. .................................................... 424/85.2
[58] Field of Search ........................................ 424/85.2

[56] References Cited

U.S. PATENT DOCUMENTS 5,124,145  6/1992  Sordillo et al. .................... 424/85.5

OTHER PUBLICATIONS

Nickerson et al. J. Dairy Sci. 72:1764–1773 (1989).
Smith et al. J. Dairy Res. 35:287–290 (1968).
Bovine Natural Cell Mediated Cytotoxicity (NCMC): Activation by Cytokines. Veterinary Immunology and Immunopathology, 24 (1990) 113–124. J. Jensen and R. D. Schultz.
Cloning, Sequence and Expression of Two Distinct Human Interleukin-1 Complementary DNAs. Nature vol. 351 (1985) 641–647 Carl J. March et al.
Frequency of Isolation of Environmental Mastitis-Causing Pathogens and Incidence of New Intramammary Infection During the Nonlactating Period. Am J Vet Res, vol. 49: No. 11, (1988) 1789–1793 S. P. Oliver.
Cytokines: Applications in Domestic Food Animals, Journal of Dairy Science vol. 74, No. 1 (1991) 328–339, Frank Blecha.
Infection of Rabbit Mammary Glands with Ovine Mastitis Bacterial Strains, J. Comp. Path. (1991) vol. 104:289–302 B. Amorena et al.
Identification of a Positive Retroregulator that Stabilizes mRNAs in Bacteria, Proc. Natl. Acad. Sci. vol. 83, 3233–3237 (1986), Hing C. Wong and Shing Chang.
Bovine GM-CSF Molecular Cloning and Biological Activity of the Recombinant Protein, Molecular Immunology, vol. 25, No. 9: 843–850 (1988), Charles R. Maliszewski et al.

Primary Examiner—Michael G. Wityshyn
Assistant Examiner—Choon P. Koh
Attorney, Agent, or Firm—Estelle J. Tsevdos

[57] ABSTRACT

Cytokines are useful for the ability to improve the natural defense system of the involuting mammary gland. In addition to the immunopotentiating activity, cytokines accelerate the normal physiology of involution of the mammary gland and thereby afford further protection against new infections of mammals. The involuting mammary gland is very susceptible to infection during the early stages of involution and therefore decreasing the period of highest susceptibility while also improving the natural defense mechanisms is of great advantage over most therapies. Used alone, in various cytokine combinations, or in combination with other therapeutics, cytokines protect the mammary gland and cure existing infections and are particularly useful during cessation of lactation and early reinitiating of lactation.

4 Claims, 9 Drawing Sheets

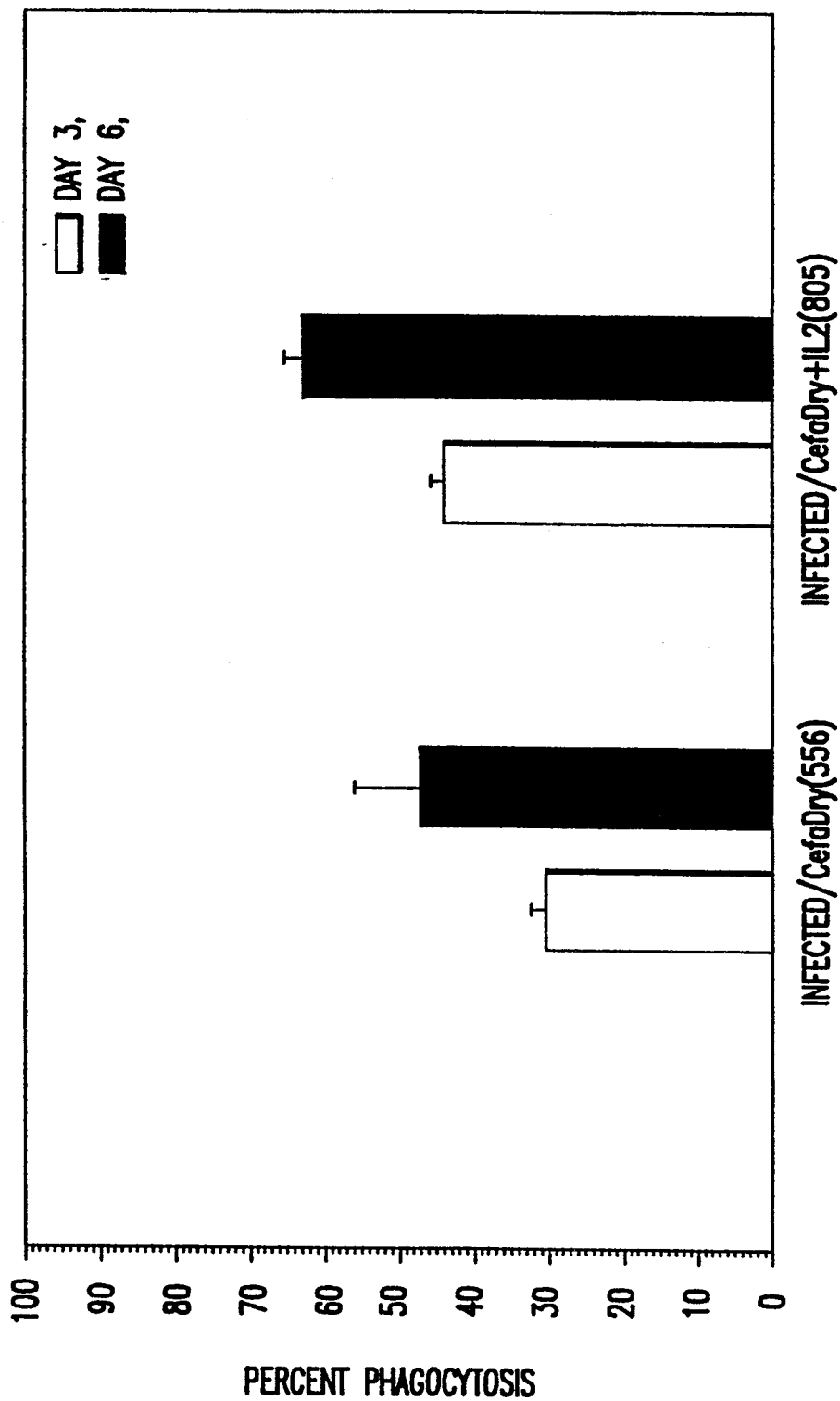

METHOD OF TREATING OR PREVENTING MASTITIS IN ANIMALS WITH INVOLUTING MAMMARY GLANDS BY ADMINISTERING RECOMBINANT CYTOKINES

This is a continuation of co-pending application Ser. No. 07/741,278 filed on Aug. 7, 1991.

BACKGROUND OF THE INVENTION

The present invention relates to the treatment or prevention of mastitis in warm-blooded animals in early lactation and/or with involuting mammary glands. The treatment utilizes recombinant cytokines.

The cytokines provide a useful therapy that significantly protects and treats the mammary gland from new or existing infections during the early stages of mammary gland involution, as well as during initiation of lactation. This therapy also improves milk production in subsequent lactation cycles. Contrary to immunization and vaccine approaches, the present invention optimizes the specific and non-specific defense mechanisms of the host to prevent the establishment of any new infections, as well as accelerating the normal physiological process of mammary gland involution. As such, the present invention is useful in effectively preventing and treating pathological infections of all mammals, but especially in milk-producing warm-blooded animals such as cattle, sheep, goats or buffalo. Furthermore, cytokine usage as an adjunct therapy with conventional antibiotic treatment of diseases is useful in decreasing incidence of new infections; improving efficacy; and/or decreasing the amount of antibiotic required for therapy, thereby reducing drug residue.

One such disease of commercial significance is mastitis, an inflammation of the mammary tissue. This disease has a variety of bacterial etiologies and causes great losses in milk production annually. Mammary gland infections are a useful model to study a variety of infectious diseases of organ systems of warm-blood animals, one of which is mastitis. Although intramammary antibiotic therapy is used in the lactating gland, one of the most effective mastitis therapies is intramammary infusion of antibiotics at the end of lactation (drying-off). This therapy can be quite efficacious in curing existing infections at the time of the drying-off.

Cytokines have a positive immunomodulatory effect on the host's immune system as well as influencing the normal biological processes of an involuting gland. The present invention significantly prevents the establishment and frequency of new bacterial infections in involuting mammary glands of mammals. Furthermore, as an adjunct to current antimicrobial therapy in the dry cow, the method of the present invention is useful in improving efficacy, reducing the dose of treatment and minimizing drug residues. Furthermore, the method of the present invention is effective against infections which have developed resistance to classical antimicrobial therapy.

A total of 12 mammary glands from normal lactating Holstein dairy cattle are infused through the teat canal with either 200 μg of r-BoIL-1; 2 mg of r-BoIL-2; or 1 mg of r-BoGM-CSF. Milk samples are collected and the number of viable somatic cells counted on a Coulter ® ZM with a C256 Channelyzer. The data is expressed as the somatic cell count per ml of milk sampled at 16, 40, 64 and 88 hours after infusion for r-BoIL-1 (A); r-BoIL-2 (D); or r-BoGM-CSF(G). The total percentage of phagocytosis by milk PMNs (polymorphonuclear cells) is quantitatively measured by flow cytometry by measuring the percentage of cells ingesting 2μ fluorescent beads for r-BoIL-1 (B); r-BoIL-2(E); or r-BoGM-CSF(H). The total population is first gated by forward angle light scatter, FALS and 90° light scatter to only consider viable polymorphonuclear cells. The induction of superoxide after PMA (520$\eta$g)stimulation is also monitored using a whole cell cytochrome-c reduction assay, for r-BoIL-1 (C); r-BoIL-2(F); or r-BoGM-CSF(I). PMNs from untreated milk could not be induced to produce superoxide, while peripheral blood PMNs are inducible in a range of 5–15 $\eta$M $O_2$/Minute/$10^7$ PMNs.

Figure 3A:
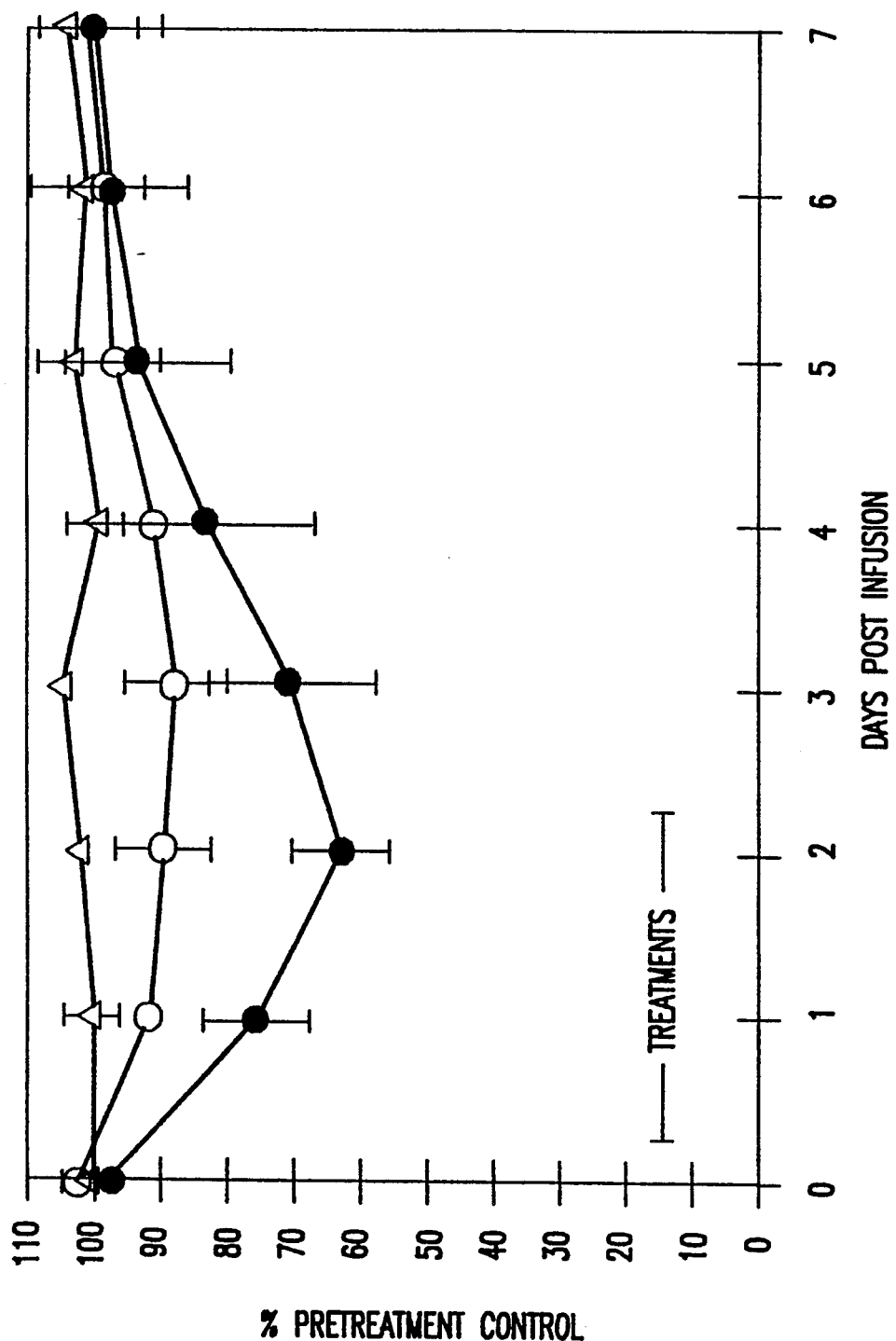
Figure 3B:
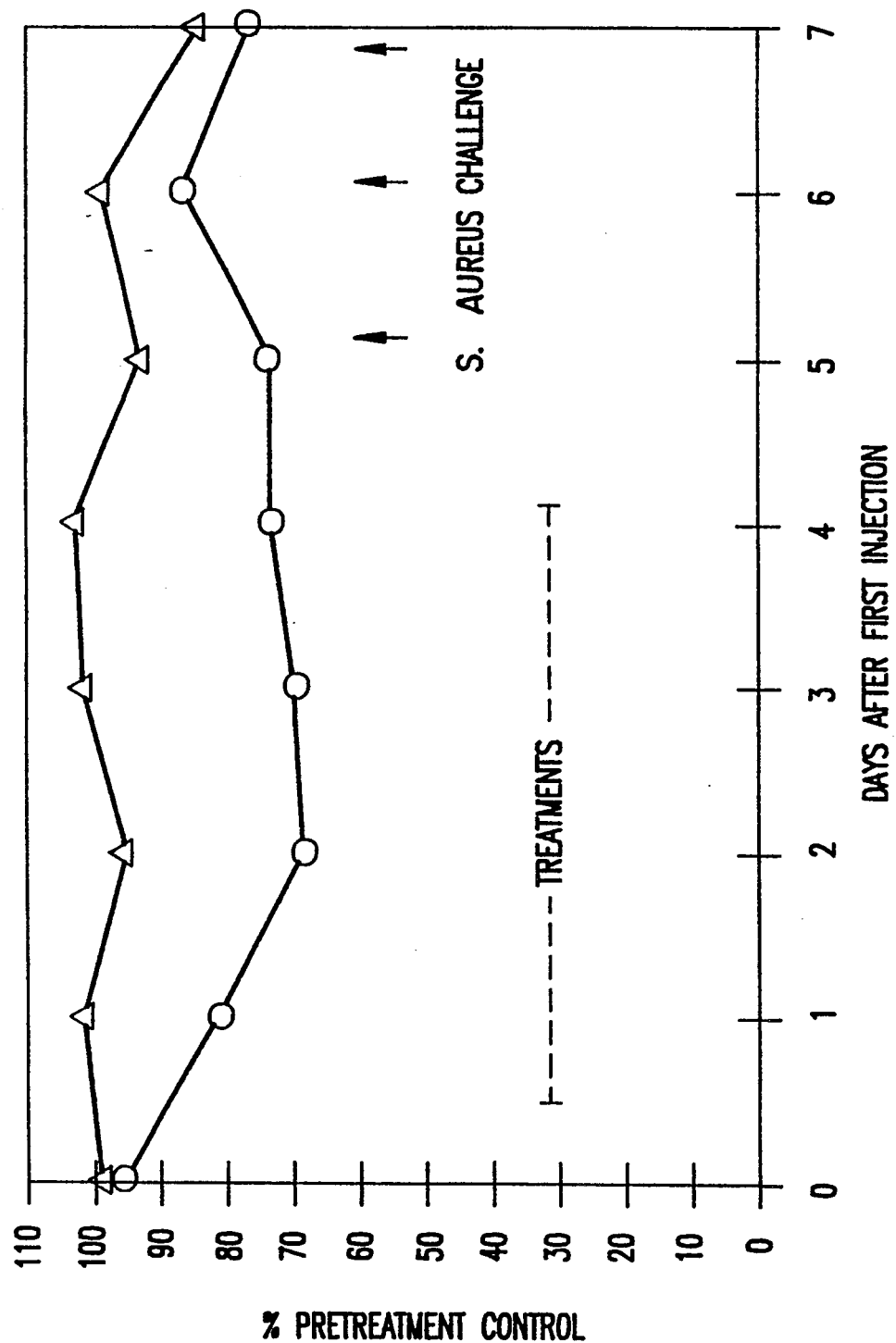

FIGS. 3(A–I): Milk Production After Intramammary Infusion or Intramuscular Injection of r-BoIL-2 into Lactating Dairy Cows Mean milk production in kilograms +/− Standard Error is recorded for 8 lactating dairy cows after intramammary infusion of r-BoIL-2 or no treatment. Data is shown as a percentage of the average milk production (Standard Deviation) compared to the first five days prior to Treatment (mean for 100% production level). Production after r-BoIL-2 intramammary infusion with total dosing amounting to 4.5 mg(o—o) or 13.5 mg(•—•) in quarters infected with S. aureaus is compared to infected, untreated cows(▲—▲) for a 6 day time period, panel A. Similarly, production is also followed in 7 lactating injections of r-BoIL-2 at 2.5 μg/kg/day for 5 days(o—o)and compared to 3 normal PBS injected controls(▲—▲), panel B. All cows are in mid to late stages of their second or third lactation at the time of r-BoIL-2 therapy. All effects on milk production are transient, returning to pre-treatment levels within 96 hours after cessation of treatment.

Figure 4A:
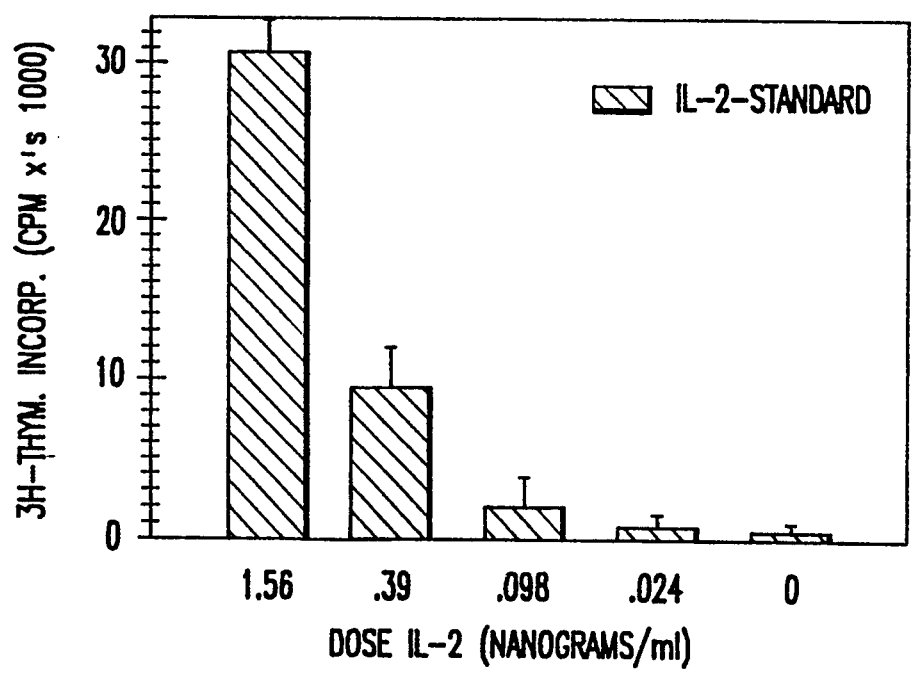
Figure 4B:
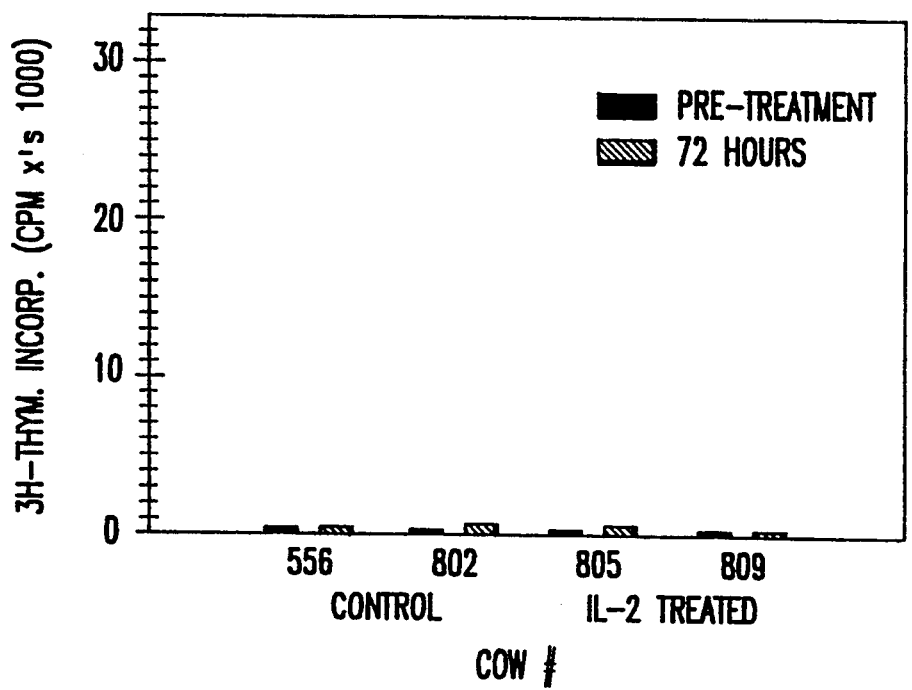

FIGS. 4(A–B): Measurement of Residual r-BoIL-2 Bioactivity in Secretions from Dry Cow Glands Infused with r-BoIL-2

Secretions from 4 quarters (4 different cows) are infused with 1 mg of r-BoIL-2 at drying-off (2 quarters) or not treated with r-BoIL-2 (2 quarters). Dry gland secretions are collected at time 0,72,144 and 240 hours after infusion. All samples shown are from the 72 hour time point and are diluted 1:50 and 1:200, and assayed for amount of biologically active r-BoIL-2 using the IL-2 dependant BT-2 T cell line, panel B. The BT-2 cell line is a bovine T cell line which requires IL-2 for growth. By measuring the degree of proliferation of this cell line, one directly measures the amount of biologically active IL-2 in a test media. Data is expressed as a mean $^3$H-thymidine incorporation $+/-$ S.D. of triplicate samples of BT-2 cells for each of the individual numbered animals. No r-BoIL-2 activity could be detected at any time point in quarters from control animals (Cow #556 & #802) or in the quarters of r-BoIL-2 treated animals (Cow #805 & #809). A standard assay of various concentrations of r-BoIL-2 in 2% dry secretions is also shown in panel A as a positive control.

FIG. 5: Phagocytic Ability of PMNs After Cytokine Administration from Mammary Glands Early in Involution A total of 4 mammary glands from 2 Holstein dairy cattle just entering the dry period are used. All quarters had been infected with S. aureaus for 4–6 weeks prior to treatment. Two of the quarters are treated with Cefa-Dri® and 2 quarters are treated with Cefa-Dri®+1 mg bovine IL-2 by intramammary infusion immediately following the last milking prior to drying-off. Dry cow secretions are then collected at day 3 and day 6 of the dry-off period and the number of viable somatic cells counted on a Coulter® with a C256 Channelyzer. The total percentage of phagocytosis by PMNs is quantitatively measured by flow cytometry by measuring the percentage of cells ingesting $2\mu$ fluorescent beads.

Figure 6:
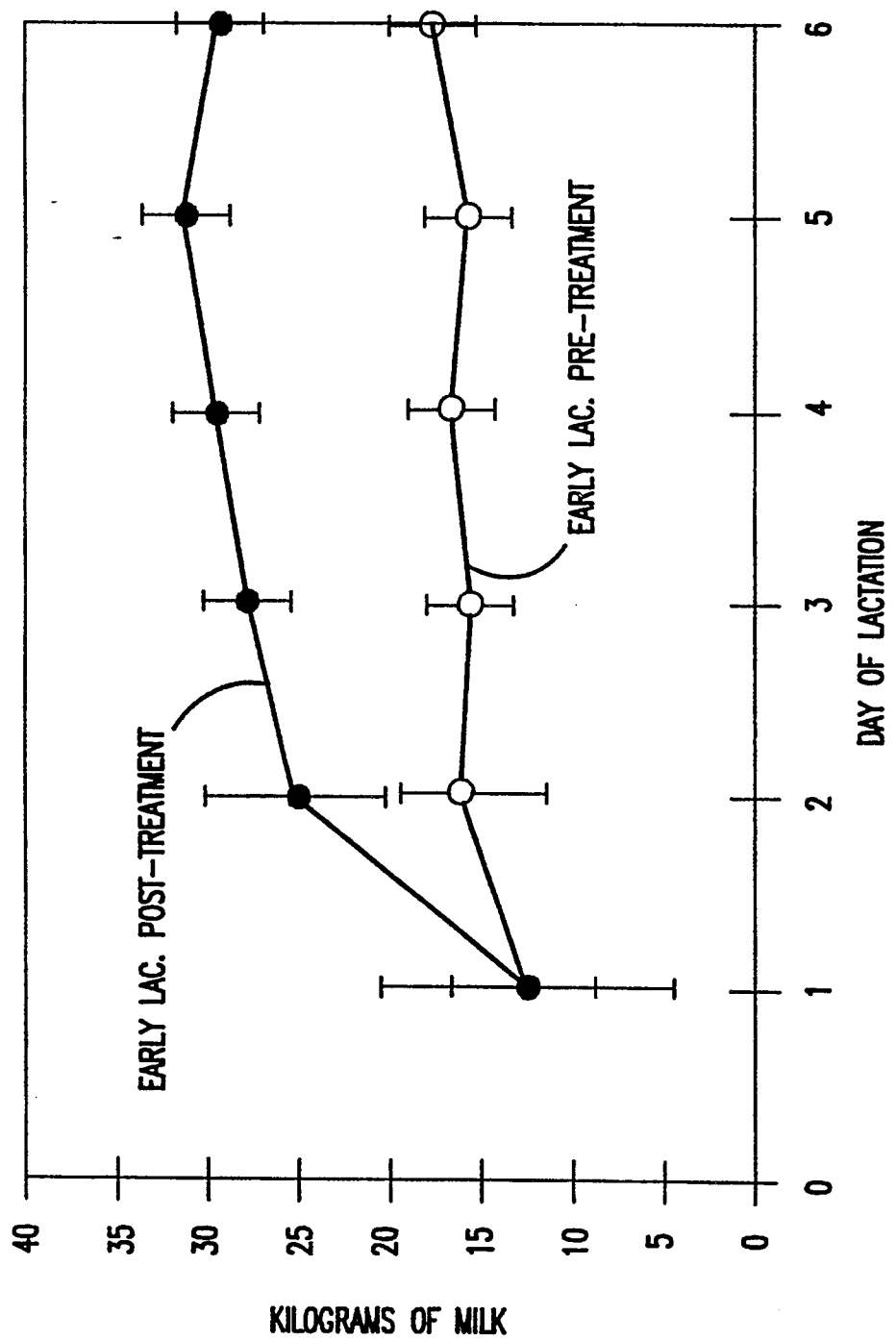

FIG. 6: Milk Production Early in Lactation Before and After Intramammary Infusion of r-BoIL-2 as a Dry Cow Therapy Mean milk production in kilograms; (S.D.) is shown for 4 cows for the first six days after the initiation of lactation for the lactation immediately prior to treatment and immediately following treatment. Production after r-BoIL-2 treatment(●-●) or for the same time period for the lactation prior to treatment(o-o) is monitored. Total dose of r-BoIL-2 received by each treated cow is 2 mg. Three cows are completing their second lactation and one is completing its third lactation at the time of r-BoIL-2 therapy. Post-treatment production from initiation of the third or fourth lactation is compared to the production for the first 6 days after initiation of the second or third lactation (pre-treatment) respectively of the same animals.

SUMMARY OF THE INVENTION

The present invention relates to the prevention or treatment of mastitis in animals during early lactations or with involuting mammary glands (dry cow therapy) by administering cytokines to an animal during said time period also known as the dry cow period. All animals infected by the mastitis causing infectious agents such as S. aureas benefit from the method of the present invention, but it is recognized that bovine, ovine and caprine animals are most often used for milk production purposes and could also benefit from such therapy.

The preferred method of the present invention encompasses administering a pharmaceutically acceptable carrier combined with various cytokines or cytokine inducers in sufficient quantity to elicit a biological response of a animal such as a warm-blooded animal when injected directly into the target tissue (intramammary) or partenterally (intramucularly or sub-cutaneously). Additionally, representative cytokines useful in the present invention include the interleukins (interleukin 1 through 12), interferens, colony stimulating factors such as granulocyte colony stimulating factor, macrophage colony stimulating factor or granulocyte macrophage colony stimulating factor, fibroblast growth factor, transforming growth factor, platelet activating factors, platelet derived growth factors or tumor necrosis factor. Further, it is contemplated that muteines of the above compounds, peptide equivalents as well as inducers thereof also are included within the scope of the present invention. Combinations of the above compounds are found to be effective in treating infections of the presently described infections: Also the case of bovine, capfine or ovine species the compound also can be directly infused through the teat canal of the mammary gland. The treatment may be repeated, especially just prior to initiation of lactation.

It is therefore an object of the present invention to provide a method for treating or preventing mastitis infections in warm-blooded animals during the dry-cow period, in early lactation and/or with involuting mammary glands. It is a further object of the present prevention to provide compositions for so treating or preventing said disease. Interleukin-2 and/or granulocyte macrophage colony stimulating factors are useful such cytokines delivered in the compositions of the present invention.

These and other objects of the invention are disclosed in the following more detailed examples in the description of the invention, which examples are illustrative and not limitative of the present invention.

DETAILED DESCRIPTION OF THE INVENTION

EXAMPLE 1

Dose Response and Biological Response of Cytokines to Intramammary Infusion

Figure 1:
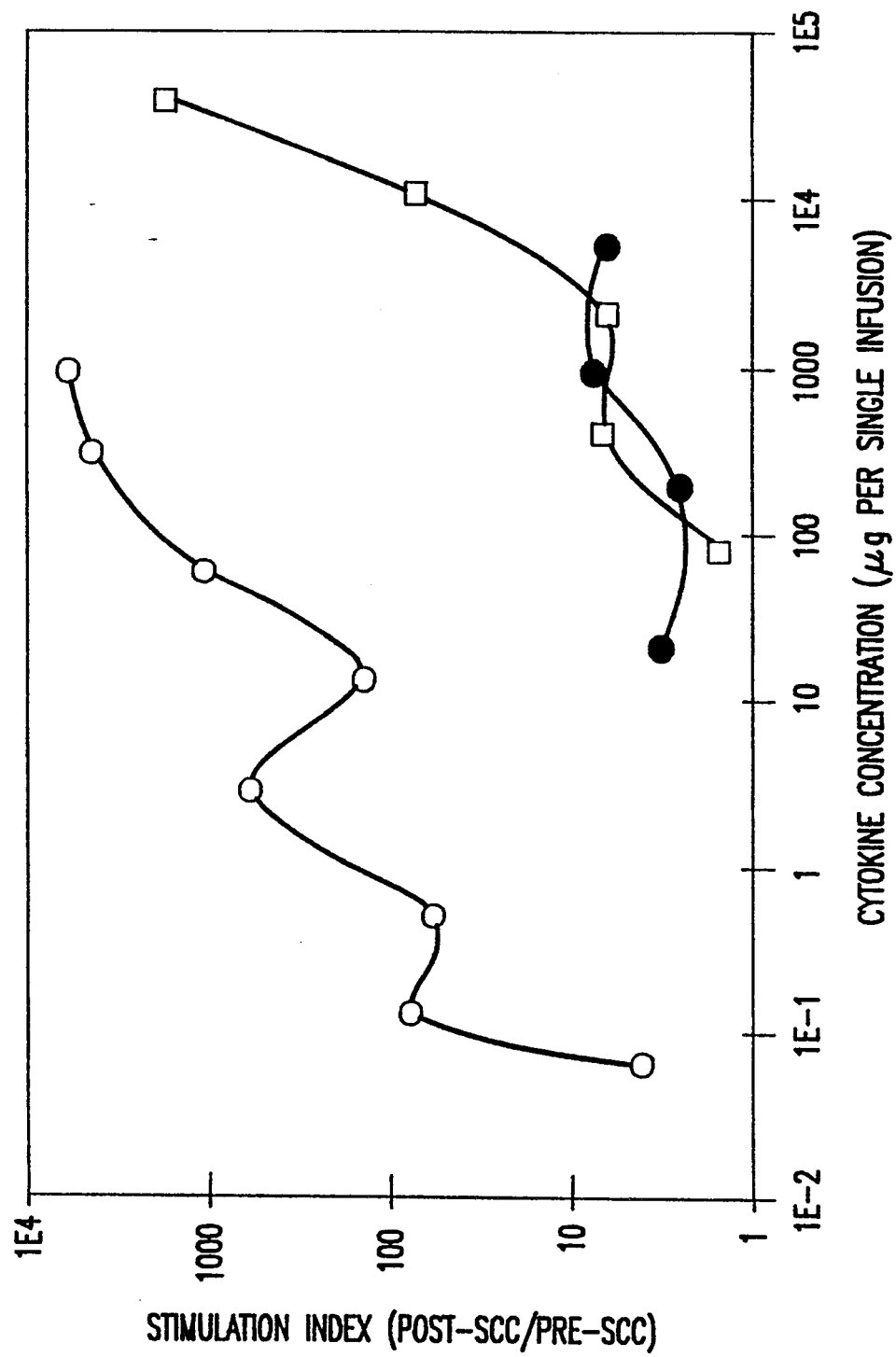
FIG. 1: Dose Response of Bovine Mammary Gland to Intramammary Infusion of Recombinant Cytokines Five fold serial dilutions of r-BoIL-1 (recombinant bovine interleukin-1) from 312.5 μg to 0.5 mg(o—o); r-BoIL-2 (recombinant bovine interleukin-2) from 40 mg to 0.1 mg(▫–▫); and r-BoGM-CSF (recombinant bovine granulocyte macrophage colony stimulating factor) from 0.2 mg to 5.0(•—•) total dose are administered at time 0 into 3-4 mammary glands from normal lactating Holstein dairy cattle. A total of 54 mammary gland quarters, 3-4 per group, are infused through the teat canal with various concentrations of recombinant bovine cytokines after the morning milking. Milk samples are collected and the number of viable somatic cells counted on a Coulter ® ZM with a C256 Channelyzer. The data is expressed as the somatic cell count per ml of milk FIGS. 2(A–I): Quantity and Quality of Milk PMNs from Mammary Glands Infused with r-BoIL-1 or r-BoIL-2

Both r-BoIL-1 and r-BoIL-2 induce an infiltration of somatic cells into the milk in a dose related manner, while r-BoGM-CSF demonstrates no significant chemoattractant activity, FIG. 1. The minimal effective dose and maximal tolerable dose for r-BoIL-1 and r-BoIL-2 is 0.5 mg to 1000 mg and 0.5 mg to 30 mg respectively, while intramammary infusion of up to 5 mg of r-BoGM-CSF fails to elicit any significant influx of cells into the mammary gland. These doses are guidelines for quantitative induction of somatic cells, but significant beneficial qualitative changes can be induced with lower doses. The specific biological activity for r-BoIL-1 as a chemoattractant is approximately 10,000 fold greater than r-BoIL-2, although the in vitro specific bioactivities are equivalent. Active IL-2 inhibition or decreased biostability in milk might explain this discrepancy. The peak number of cells after r-BoIL-1 infusion with a maximal tolerable dose is 4–5 fold greater than r-BoIL-2. The kinetics of PMN migration into the mammary gland is such that migration occurs 8–24 hours sooner for r-BoIL-1 infusions or the BoIL-2 infusion depending upon the dose. The dominant cell type after r-BoIL-1 or r-BoIL-2 infusion is PMNs.

Figure 2A:
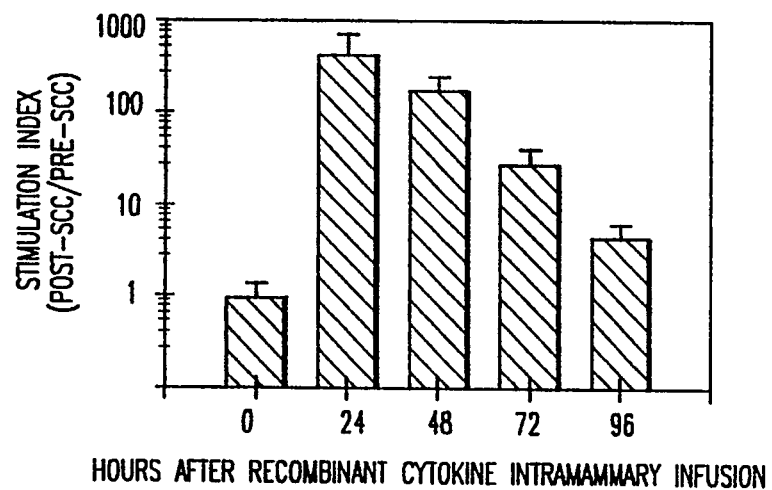
Figure 2B:
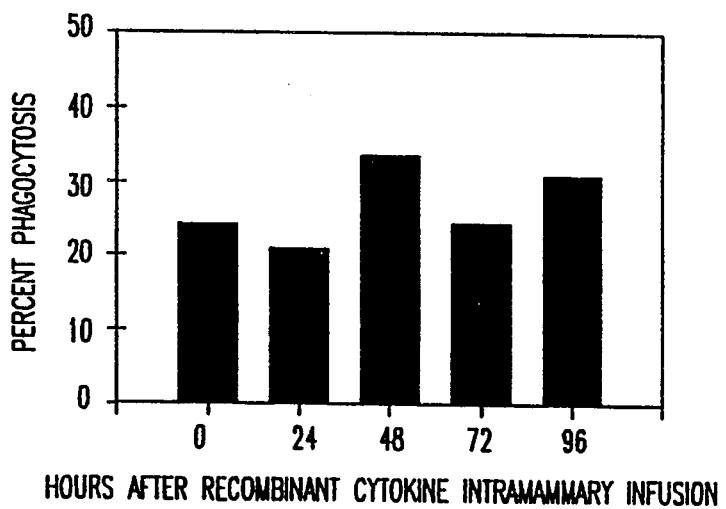
Figure 2C:
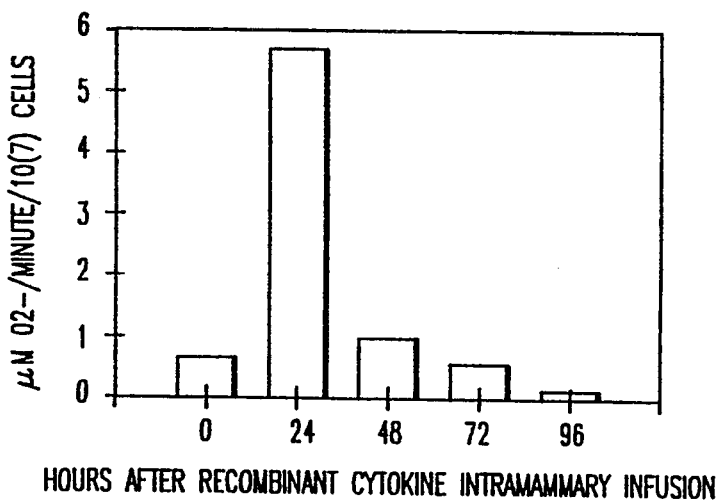
Figure 2D:
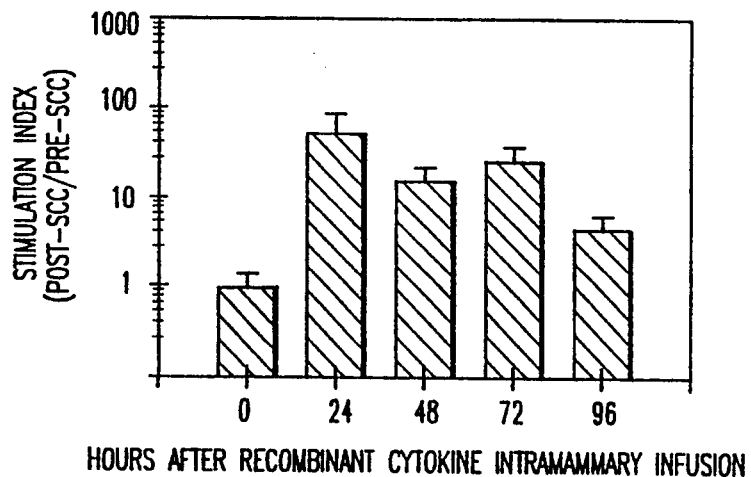
Figure 2E:
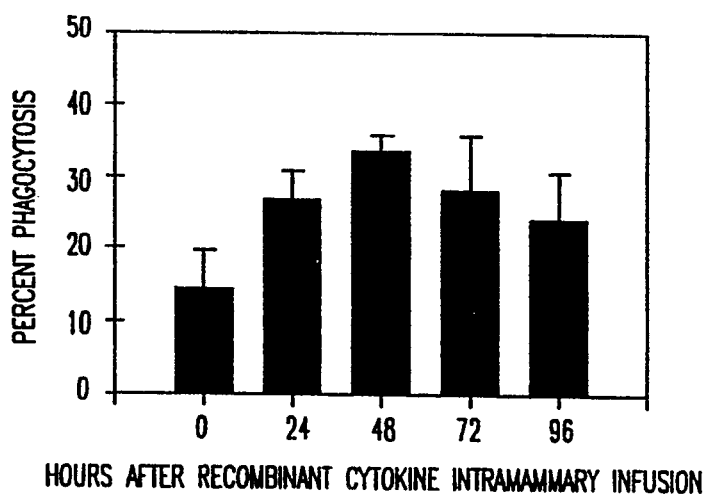
Figure 2F:
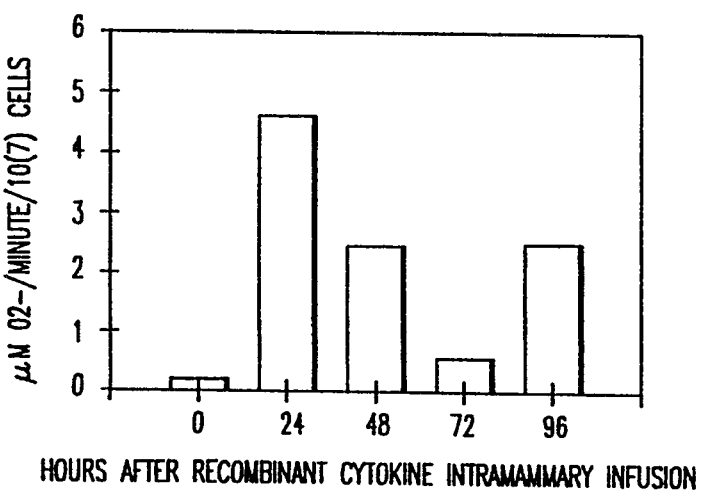
Figure 2G:
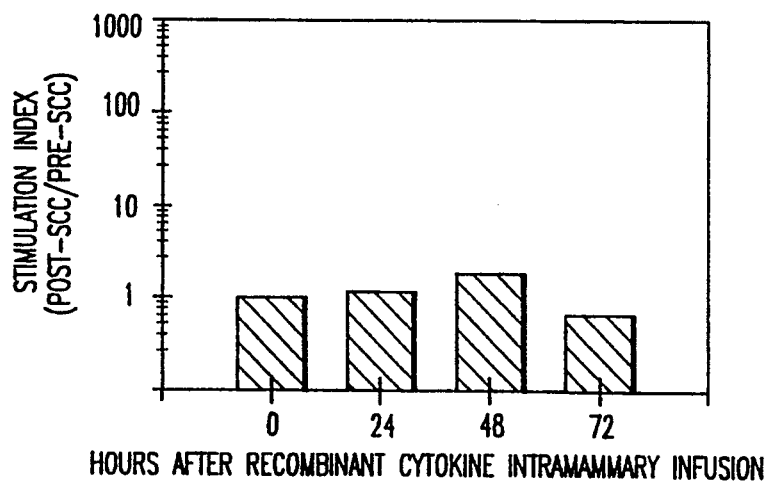
Figure 2H:
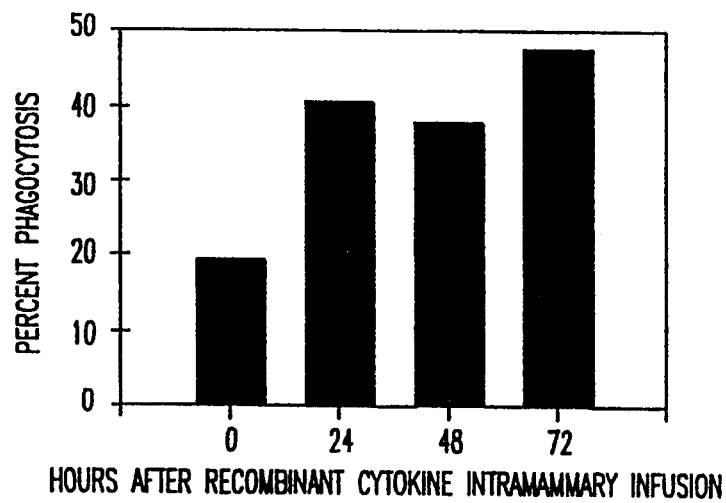
Figure 2I:
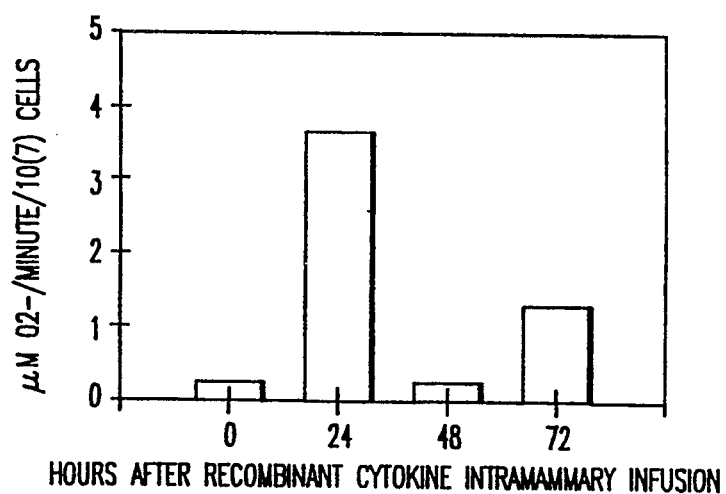

In addition to quantitative changes in milk PMNs after cytokine infusion, qualitative changes (activation) are also observed. r-BoIL-1 induces an initial 150× increase over the pre-treatment number of PMNs at 16 hours, decreasing to 20× at 40 hours, and back to normal levels by 112 hours, FIG. 2A. The inducible superoxide upon phorbol ester stimulation is significantly increased over the resident PMNs, FIG. 2C. The inducible superoxide from resident milk PMNs is significantly inhibited and is only 5% of that from peripheral blood PMNs from the same animal. Phagocytosis is unaffected by intramammary r-SoIL-1 administration, FIG. 2B, perhaps suggesting that the recruited PMNs are only partially activated or primed.

r-BoIL-2 administration also elicit a quantitative increase in milk PMNs, FIG. 2D, which diminishes after 72 hours, to control levels at the 2 mg dose. As with r-BoIL-1 administration, inducible superoxide is significantly increased over the resident PMNs, FIG. 2F, and remains throughout the 96 hours of sampling. Phagocytosis is increased 2-3 fold over resident PMNs within the 40-64 hours after time point and although the percent phagocytosis tapers off by 112 hrs, it is still above the pre-treatment level, FIG. 2E. The average number of ingested beads per phagocytic cell is also increased upon activation. The delay of peak phagocytic activity, as compared to somatic cell counts, suggests that activation and chemoattraction can be distinctly regulated.

r-BoGM-CSF fails to elicit any significant quantitative increase in milk PMNs, FIG. 2G, even with a 5 mg intramammary dose. However, the biological activity, as measured by inducible superoxide production is increased over the resident PMNs, FIG. 2I. Further, the percent of cells which are phagocytic, are enhanced, FIG. 2H. The increase in phagocytosis is maintained above pre-infusion levels for up to 112 hrs.

EXAMPLE 2

Milk Production in Lactating Glands After Intramammary Infusion

In vivo measurement of daily milk production is also monitored for both intramammary infusions and intramuscular injection. Cows are milked morning and evening and the milk weighed and recorded in total kilograms per day. The total dose of IL-2 administered per cow ranges from 2 to 96 mg. Single or multiple intramammary infusions of IL-2 have variable effects on individual animal's milk production based upon the total dose of r-BoIL-2 administered per day, FIG. 3 A (INTRAMAMMARY). Production decreases as much as 30-40% by the third infusion in the high dose animals (13.5 mg), whereas only a 12% decrease is observed at the 4.5 mg dose (not statistically different from time 0 production or control animals). No statistically significant effect on milk production has been observed if the total dose is less than 4.5 mg. This suggests that the secretary epithelium of the mammary gland can be induced to a physiological state of non-secretion by cytokines. This induction would be of great significance to assist in the morphological changes required during early lactation and serves to accelerate the protective mechanisms. Similar effects on milk production are observed with intramuscular injection of r-BoIL-2 at 2.5 μg/kg body weight/day for 5 days, FIG. 3 B (INTRAMUSCULAR).

EXAMPLE 3

Pharmacokinetics of Cytokine Administration to Dry Cows

To specifically study the presence of cytokines after a single intramammary infusion into dry cows, 5 quarters from four different cows, are infused with 1 mg r-BoIL-2 at dry-off. Since a dry gland does not have its contents milked out every 12 hours, the retention of biological activity of r-BoIL-2 infused into the dry gland at 72 hours or greater is examined. Secretions from dry cow quarters treated with 1 mg of r-BoIL-2 are collected at 72, 144 and 240 hours after dry cow treatment. As with the milk, a 1:50 dilution of dry secretion samples is made and these solutions assayed by the bioassay using BT-2 and compared to r-BoIL-2 diluted in media. As shown in FIG. 4, no detectable r-BoIL-2 bioactivity (less than 0.024 ηg/ml) is demonstrated in treated glands as early as 72 hours after infusion. Therefore, cytokines exert a beneficial long-term change in the protective mechanisms of the gland which significantly exceeds the time limit of detection for biological activity in the gland.

EXAMPLE 4

Prevention of Mastitis in Lactating Animals

The potential benefits of exogenous cytokine administration to the host, as it relates to the differential induction of quantitative and qualitative changes in milk PMNs, is further explored in applied preventative and therapeutic experiments. r-BoIL-l, r-BoIL-2 and r-BoGM-CSF are all capable of protecting the host from subsequent *S. aureus* challenge, Table 1. The protective effect of r-BoIL-1 is most efficacious if administered 24 hours prior to *S. aureus* challenge. This maximal protection correlates with the peak quantitative biological response for this cytokine. The protective effect of r-BoIL-2 is most efficacious if administered 48 hours prior to *S. aureus* challenge. This also correlates with the peak quantitative biological response of this cytokine and also marks the qualitative increase in phagocytosis and inducible superoxide, FIG. 2D & 2E. Unlike r-BoIL-1 and r-BoIL-2, r-BoGM-CSF elicit only minor quantitative changes in milk PMNs. However, good protection from *S. aureus* is observed when r-BoGM-CSF is administered both 24 and 48 hours prior to challenge. Both these time periods are shown to increase phagocytic ability of the cells in the milk of treated glands, FIG. 2H.

TABLE 1

Prevention of *S. aureus* Mastitis by Recombinant Bovine Cytokines

| TREATMENT[1] | GLANDS[2] | DOSE[3] | ADMINISTRATION[4] | % INFECTED[5] | % CONTROL[6] |
|---|---|---|---|---|---|
| CONTROL 1* | 10 | — | — | 100 | 0 |
| IL-1 | 10 | 1 μg | 0 hrs | 13 | 87 |
| | 10 | " | −24 hrs | 0 | 100 |
| | 10 | " | −48 hrs | 22 | 78 |
| IL-2 | 10 | 1 mg | 0 hrs | 77 | 23 |
| | 10 | " | −24 hrs | 11 | 89 |
| | 10 | " | −48 hrs | 37 | 63 |
| CONTROL 2* | 10 | — | — | 82 | 0 |
| GM-CSF | 10 | 1 mg | −24 hrs | 20 | 76 |

TABLE 1-continued

| | Prevention of *S. aureus* Mastitis by Recombinant Bovine Cytokines | | | | |
|---|---|---|---|---|---|
| TREATMENT[1] | GLANDS[2] | DOSE[3] | ADMINISTRATION[4] | % INFECTED[5] | % CONTROL[6] |
| | 10 | " | −48 hrs | 20 | 76 |

[1] Single intramammary infusion administered after the PM milking. A total of 100 mammary glands from 22 different lactating Holstein dairy cattle are treated.
[2] All glands are free of bacteria on 5 successive samples after the AM milking prior to the initial infusion.
[3] The total dose in mass of protein is indicated. The biological activity of r-BoIL-1, r-BoIL-2 and r-BoGM-CSF are 32,000 Units/μg, 22,000 Units/μg and 38,000 Units/μg respectively.
[4] Infusions of cytokines were administerd simultaneously with *S. aureus* 0, 24 or 48 hours proir to challenge with 30–200 CFUs of *S. aureus*.
[5] Individual quarters are considered cured if the milk samples remain free of *S. aureus* for 14 days after intramammary challenge with of *S. aureus*.
[6] The % Control = (1 − {% Infected After Therapy divided by Infected in Control Quarters}) × 100.
*Quarters in Control 1 are challenged with 250 CFUs of *S. aureus*. Quarters in Control 2 are challenged with 30 CFUs of *S. aureus*.

EXAMPLE 5

Therapy of Established Infections with Cytokines

Infected mammary glands are also effectively treated with intramammary infusion of r-BoIL-1 and r-BoIL-2, see Table 2. Both cytokines have a dose response therapeutic efficacy. r-BoIL-1 and r-BoIL-2 are most efficacious if doses are administered over 3 consecutive milkings, rather than in a single bolus. The percentage of quarters clearing the infection for greater than 1 milking (RESPONDING), as compared to the percentage of quarters which actually cure their infections (CURE) is a measure of the failure of the host cells to kill the bacteria. The relapse rate is the greatest for r-BoIL-2 (combined relapse rate of 40% for the 10 mg dose X's 3). The high relapse rate for r-BoIL-1 suggests that although many host cells may indeed ingest *S. aureus*, these cells are inefficient at killing the bacteria. The relapse rate for r-BoIL-1 (54%) is comparable to the Na (sodium) cephapirin treatment (57%), while the relapse rate for r-BoIL-1 (54%) is more closely approximated by the Cefa-Lak ® treatment (16%), albeit the overall cure rates are not as efficacious as Cefa-Lak ®. This suggests that activation of phagocytic cells in the milk is an essential component of effective therapy for infectious agents. Furthermore, if activation of the host cells is effective, as indicated by the r-BoIL-2 and r-BoGM-CSF, then a combination therapy with r-BoIL-1 or antibiotics is useful.

The biological activity of PMNs and number of PMNs during mastitis infections are both variable, both within the animal and in each individual infected gland. Clearly, activation of phagocytosis is necessary to efficiently eliminate bacteria but is insufficient without proper activation of the bactericidal components of the phagocytic cell. Such a dissociation of activation of phagocytosis without activation of bactericidal activity could in fact contribute to a source of reinfection as stated earlier. This biological activity can be precisely modulated by local in vivo administration of recombinant homologous cytokines to a targeted organ.

TABLE 2

| | Efficacy of Recombinant Bovine Cytokines as Mastitis Therapeutics | | | | |
|---|---|---|---|---|---|
| TREATMENT[1] | DOSE[2] | INTERVAL | % RESPONSE[3] | % CURES[4] | % RELAPSE[5] |
| IL-1 (single) | 10 μg | — | 11 | 11 | 0 |
| | 200 μg | — | 20 | 0 | 100 |
| | 600 μg | — | 10 | 0 | 100 |
| IL-1 (multiple) | 10 μg | 24 hrs | 77 | 8 | 90 |
| | 10 μg | 48 hrs | 39 | 0 | 100 |
| | 200 μg | 24 hrs | 79 | 7 | 91 |
| | 200 μg | 48 hrs | 64 | 29 | 54 |
| IL-2 (single) | 2 μg | — | 0 | 0 | — |
| | 10 μg | — | 20 | 0 | 100 |
| | 30 μg | — | 10 | 10 | 0 |
| IL-2 (multiple) | 2 mg | 24 hrs | 55 | 9 | 84 |
| | 10 mg | 48 hrs | 33 | 8 | 76 |
| | 10 mg | 24 hrs | 58 | 25 | 57 |
| | 10 mg | 48 hrs | 33 | 25 | 23 |
| Na Cephapirin | 200 mg | 12 hrs | 86 | 42 | 51 |
| Cefa-Lak ® | 200 mg | 12 hrs | 92 | 77 | 16 |

[1] *S. aureus* infections are established 2–3 weeks prior to treatment. Treatments are administered after the AM or PM milking by 1–3 successive intramammary infusions. A total of 120 mammary glands from 28 different lactating Holstein dairy cattle are used. Recombinant bovine interleukin-1(IL-1) and interleukin-2(IL-2) are obtained from IMMUNEX Corp., Seattle, WA. Na cephapirin is prepared is PBS; and Cefa-Lak ® (Bristol-Meyers) is used according to package insert instructions.
[2] Cytokines are infused intramammary through the teat canal after the PM milking at the indicated intervals. The total dose is delivered in a total volume of 10 ml of sterile PBS. The biological activity of r-BoIL-1 and r-BoIL-2 is 32,000 Units/μg and 22,000 Units/μg, respectively. A total dose per infusion 200 mg of Na cephapirin and Cefa-Lak ® is administered after consecutive PM and AM milkings, according to described procedures.
[3] The % RESPONDING = quarters which transiently (> 1 milking) are free of *S. aureus* divided by the total number of quarters treated.
[4] The % CURED QUARTERS = # of quarters which clear their infection and remain free of *S. aureus* divided by the total number of quarters treated. Infections are considered to have relapsed if there are > 1 CFUs from three consecutive AM milkings, or > 20 CFUs for two consecutive after therapy at anytime during the 14 day monitoring period.
[5] The % RELAPSE = [1 − {% RESPONDING divided by % CURED}] × 100.

EXAMPLE 6

Phagocytic Activity of Cells from Dry Cow Secretions after Cytokine Treatment Somatic cells are isolated from mammary gland lavages on days 3 and 6 after treatment with Cefa-Dri ® plu6 IL-2 or Cefa-Dri ® alone. The cells are incubated with fluorescent latex microspheres and analyzed on the flow cytometer for their ability to phagocytize the beads. FIG. 5 shows that phagocytic activity increases on day 6 as compared to day 3 in the infected quarters for both treatment groups and yet no biologically active IL-2 is detected after 3 days, FIG. 4. In contrast, phagocytic activity decreases in the uninfected quarters on day 6 as compared to day 3 for both treatment groups. This data suggests that cells from glands with an established infection at the time of dry-off maintain a higher level of phagocytic activity than cells from glands that are clear of infection at the time of dry-off. Also, treatment with IL-2 seems to enhance the phagocytic activity of cells of the dry gland.

EXAMPLE 7

Prevention of Nocardia Infections by Treatment with Cytokines

Two groups of 17 mammary quarters from 10 different Holstein dairy cows are assigned to receive routine dry cow therapy Cefa-Dri ® or dry cow therapy plus 1 mg of recombinant bovine interleukin-2 (IL-2). Antibiotic treatment of Nocardia infections has been shown to be ineffective. Cefa-Dri ® treated quarters result in 72% of the glands becoming infected with Nocardia after challenge with broth dipping, Table 3. However, only 53% of the glands become infected if the dry cow therapy includes recombinant IL-2.

re-challenged with 50-250 CFU of S. aureus and the animals allowed to calf. Upon the initiation of lactation, samples are taken on three successive milkings and tested for the presence of S. aureus. All quarters treated with Cefa-Dri ® alone are found to be infected. However, 40% of the Cefa-Dri ® plus IL-2 treated quarters are free of infection at initiation of lactation, Table 4.

TABLE 4

Prevention of S. aureus Infections By r-BoIL-2 After Chalenge During Dry Period
PERCENT QUARTERS INFECTED[1]

| TREATMENT[2] | #GLANDS | IL-2 DOSE[3] | DRY-OFF | D/O + 10 DAYS[4] | Calving + 5 Days[5] |
|---|---|---|---|---|---|
| Cefa-Dri ® | 10 | — | 100 | 0 | 100 |
| Cefa-Dri ® + rBoIL-2 | 10 | 1 mg | 100 | 0 | 60 |

[1] All quarters are all infected with Staphylococcus aureus (New bould strain 305) for a minimum of 2 weeks prior to drying-off.
[2] Single intramammary infusion is administered after the last PM milking for Cefa-Dri ®. The r-BoIL-2 treated animals were infused with r-BoIL-2 then with Cefa-Dri ®. A total of 20 mammary glands from 7 different Holstein dairy cattle entering the dry period are treated.
[3] The total dose in mass of protein is indicated. The biological activity of r-BoIL-2 is 22,000 Units/μg.
[4] All quarters are stripped at Day 10 and their dry secretions plated for the presence of S. aureus.
[5] All quarters are sampled twice 405 days after calving and the milk plated to detect the presence of S. aureus.

EXAMPLE 9

Improved Milk Production in Lactations Immediately Following Dry Cow Therapy with Cytokines The effects of r-BoIL-2 on possible milk production after dry-cow therapy are also evaluated. Milk production for three dairy cows for the first five days of the lactation cycle (second or third lactation) prior to r-BoIL-2 treatment is compared to the milk production for the first five days of the lactation cycle (third or fourth lactation) immediately following r-BoIL-2 treatment, FIG. 6. No inhibition of milk production and in fact an 80% improvement in production at the following lactation after r-BoIL-2 treatment is observed.

What is claimed is:

1. A method for increasing milk production in lactations subsequent to a warm-blooded animal's dry period, said method comprising: administering to said warm-blooded animal in the early lactation stages or stage wherein said animal has an involuting mammary gland, a interleukin-2.

2. A method according to claim 1, wherein said warm-blooded animal is bovine, ovine or caprine.

3. A method according to claim 2, wherein said interleukin-2, activates phagocytic cell function or the immune system of said animal.

4. A method according to claim 3, wherein said interleukin-2 is administered in amounts from about 0.01 mg to 40 mg per mammary quarter treated.

* * * * *

TABLE 3

PREVENTION OF NOCARDIA INFECTIONS BY r-BoIL-2 IN DRY COWS
PERCENT QUARTERS INFECTED[1]

| TREATMENT[2] | #GLANDS | IL-2 DOSE[3] | DRY-OFF | D/O + 10 DAYS[4] | D/O + 28 DAYS |
|---|---|---|---|---|---|
| Cefa-Dri ® | 17 | — | 0 | 24 | 72 |
| Cefa-Dri ® + rBoIL-2 | 17 | 1 mg | 0 | 6 | 51 |

[1] Individual quarters are dipped in broth of 10[8] cfu/ml of Nocardia at drying-off. All teats are then dipped in iodidine solution and treated with respective dry-cow therapy.
[2] Single intramammary infusion is administered after the last PM milking. A total of 34 mammary glands from 10 different Holstein dairy cattle entering the dry period are treated.
[3] The total dose in mass of protein is indicated. The biological activity of r-BoIL-2 is 22,000 Units μg. infusions of r-BoIL-2 are administered simultaneously with Cefa-Dri ®.
[4] All quarters were stripped at indicated times and their dry secretions plated for the presence of Nocardia.

EXAMPLE 8

Prevention of New Infection of Staphylococcus aureus Early in Mammary Gland Involution Two groups of 12 S. aureus infected mammary quarters from 6 different Holstein dairy cows are assigned to receive routine dry cow therapy Cefa-Dri ® or dry-cow therapy plus 1 mg of recombinant bovine interleukin-2(IL-2). 8–10 days after treatment at drying-off, dry secretion samples are taken and tested for the presence of residual antibiotics or bacteria. All quarters are then